United States Patent [19]

Raab

[11] Patent Number: 5,113,026
[45] Date of Patent: * May 12, 1992

[54] PROCESS FOR PREPARATION OF SUBSTANTIALLY FLUORINATED ALKYL BROMIDES

[75] Inventor: Klaus Raab, Burgkirchen, Fed. Rep. of Germany

[73] Assignee: Hoechst Aktiengesellschaft, Frankfurt am Main, Fed. Rep. of Germany

[*] Notice: The portion of the term of this patent subsequent to Dec. 17, 2008 has been disclaimed.

[21] Appl. No.: 713,962

[22] Filed: Jun. 11, 1991

[30] Foreign Application Priority Data

Jun. 13, 1990 [DE] Fed. Rep. of Germany ....... 4018913

[51] Int. Cl.$^5$ .............................................. C07C 17/20
[52] U.S. Cl. .................................................... 570/170
[58] Field of Search ........................................ 570/170

[56] References Cited

U.S. PATENT DOCUMENTS 2,678,953 5/1954 Conly.
2,875,253 2/1959 Barnhart.

FOREIGN PATENT DOCUMENTS 49-48286 12/1974 Japan ................................... 570/170

OTHER PUBLICATIONS

Haszeldine, R. N., *J. Chem. Soc.*:3761-3768 (1953).
Lond, D. M. et al., *Preparation, Properties anad Industrial Applications of Organofluorine Compounds*, N.Y., John Wily and Sons, 1982, p. 154.
Huang, B., et al., *Chem. Abs.* 102:78312x (1985).
Furutaka, Y., et al., Chem. Abs. 104:88106p (1986).

Primary Examiner—Alan Siegel

[57] ABSTRACT

A process for the preparation of substantially fluorinated alkyl bromides from the corresponding iodides is described. At least one anhydrous metal bromide, which can contain certain metals as the cation, is reacted at 80° to 450° C. under atmospheric pressure or the autogenous pressure of the reaction mixture and with good mixing, with the substantially fluorinated alkyl iodide, without the addition of other substances. The new process achieves good yields of substantially fluorinated alkyl bromides and requires no special safety precautions.

8 Claims, No Drawings

PROCESS FOR PREPARATION OF SUBSTANTIALLY FLUORINATED ALKYL BROMIDES

DESCRIPTION

The invention relates to a process for the preparation of substantially fluorinated alkyl bromides from substantially fluorinated alkyl iodides.

It is known from U.S. Pat. No. 2,678,953 to obtain perfluoroalkyl bromides from the anhydrous metal salts of perfluoroalkylcarboxylic acids by reaction with bromine, the conversion being increased by using visible light. In the only example the preferred silver salt is used. This process is laborious, since the perfluoroalkylcarboxylic acid must first be prepared, for example by the known reaction of perfluoroalkyl iodide with $SO_3$ or fuming sulfuric acid. The acid must then be converted into the metal salt and the latter must be dried. Furthermore, the reaction using bromine, which is toxic and corrosive, requires particular care and an increased outlay on equipment (safety precautions and corrosion). In addition, in the chain of reactions, one $CF_2$ group of the perfluoroalkyl iodide is lost.

It is also known from U.S. Pat. No. 2,875,253 to telomerize, in the presence of a peroxidic polymerization promoter, a lower hydrocarbon substituted by fluorine, bromine and, if appropriate, chlorine, as the telogen with an olefin which contains fluorine and can additionally contain chlorine atoms. Inter alia, $CF_3Br$, $CF_3BrCl$, $CF_2Br_2$, $C_2F_5Br$, $C_2F_4BrCl$, $C_3F_6BrH$ and $C_3F_6Br_2$ are mentioned as possible telogens, and tetrafluoroethylene is mentioned amongst a large number of possible olefins containing fluorine. The reaction of these compounds would have to result in substantially fluorinated alkyl bromides as defined in the present invention, but there is no example from which it would be possible to deduce under what precise conditions and with what success the reaction with tetrafluoroethylene can be carried out. In the examples, $CF_2=CFCl$ is always employed as the olefin containing fluorine.

In an article by Long, Higgins, Mattrey, Mitten and Multer on radio-opaque fluorocarbons (R.E. Banks, "Preparation, Properties and Industrial Applications of Organofluorine Compounds", 1982, Ellis Horwood Ltd. Publishers/Chichester, pages 139 to 156), it is mentioned at the end of the discussions (page 154 foot) that the perfluoro-n-hexyl bromide or perfluoroisoheptyl bromide used for the investigations was prepared by thermal bromination of the corresponding perfluoroalkyl iodides with elemental bromine, but more precise details are lacking. No doubt the difficulties with equipment, already mentioned earlier in the text, when using bromine are increased if the reaction with this corrosive substance is carried out thermally, that is to say at elevated temperatures. R. N. Haszeldine, J. Chem. Soc., 1953, pages 3,761 to 3,768 and also Huang Bingnan and Huang Weiyuan, Shanghai Inst. Org. Chem. Acad. Sinica, Huaxue Xuebao 42, pages 1,106 to 1,108 (C.A. 102; 78312x), 1984 describe the photochemical bromination of perfluoroalkyl iodides [Examples: $R_fI$ or $Cl(CF_2)_4I$] with bromine under UV irradiation. $R_fBr$ or $Cl(CF_2)_4Br$ is obtained in a very good yield after 168 hours or 50 hours, respectively. However, this process is also expensive in terms of equipment and energy.

Finally, it is known from JP preliminary published specification 60,184033-A2, 1985 (C.A. 104; 88106p) to prepare $C_nF_{2n+1}Br$ (n=6 to 11) by reacting $C_nF_{2n+1}I$ with bromine in the presence of a compound which produces free radicals (for example azodiisobutyronitrile). $C_6F_{13}Br$ is thus obtained in a yield of 40%. Here too, the use of elemental bromine requires precautions relating to the equipment.

The object of the invention is to provide a process for the preparation of substantially fluorinated alkyl bromides which gives good yields without the use of solvents, catalysts and similar additives and which does not have the difficulties involved in working with elemental bromine at elevated temperatures.

The new process for the preparation of substantially fluorinated alkyl bromides from compounds of the formula $$X-(CF_2)_n-I \qquad (I)$$

in which X is H, F, Cl, Br, I or $(CF_3)_2CF-$ and n is 2 to 16, comprises reacting, with good mixing, 1 mol of bound iodine atom in the compound of the formula (I) with 1 to 6 mol of bromide ions which are present in the form of at least one anhydrous salt selected from the group composed of: bromides of metals of groups I a, I b, II a or II b of the periodic table of the elements, $CsBr_3$, $MnBr_2$, $FeBr_2$, $FeBr_3$, $CoBr_2$, $NiBr_2$, $SnBr_2$, $PbBr_2$, $TlBr$, $IrBr$, $IrBr_2$, $PtBr_2$ or $PtBr_4$, at 80° to 450° C. under atmospheric pressure or the autogenous pressure of the reaction mixture, without the addition of other substances.

Compounds of the abovementioned formula (I) can be prepared by various known processes. For example, it is possible, by reacting iodine with iodine pentafluoride and tetrafluoroethylene, to prepare perfluoroethyl iodide, which, in turn, can be reacted by telomerization with further tetrafluoroethylene to give higher perfluoroalkyl iodides. Analogous compounds can be obtained by using appropriate starting materials. Some of the compounds of the formula (I) are commercial products. It is preferable to employ compounds of the formula (I) in which X is I, in particular those in which X is either $(CF_3)_2CF-$ or F. Compounds of the formula (I) in which n is greater than 16 generally give longer reaction times and frequently worse yields, and they are also as a rule less easy to use. Compounds of the formula (I) in which n is 4 to 12 and especially 6 to 8 are preferred because of their good applicability. It is also possible to use mixtures of compounds of the formula (I) containing different substituents X and/or different numbers n.

In accordance with the invention 1 mol of bound iodine atom of the compound of the formula (I) is reacted with 1 to 6 mol of bromide ions, which can be present in the form of salts with various cations. If less than 1 mol of bromide ion per mol of iodine atom in the compound of the formula (I) is used, poorer yields are obtained. In principle, more than 6 mol of bromide ions per mol of iodine atom in the compound of the formula (I) can be employed, but, in general, no improvement in the yield is observed as a result of this, so that this is an unnecessary expense. It is preferable to use 1.2 to 3 mol of bromide ions per mol of iodine atom in the compound of the formula (I).

The bromide ions should be present in the form of at least one anhydrous salt with a metal from groups I a, I b, II a or II b of the periodic table of the elements, for example $KBr$, $CuBr_2$, $MgBr_2$ or $ZnBr_2$, and also as $MnBr_2$, $FeBr_2$, $FeBr_3$, $CoBr_2$, $NiBr_2$, $SnBr_2$, $PbBr_2$, $TlBr$, $IrBr$, $IrBr_2$, $PtBr_2$ or $PtBr_4$. Complex metal bromides, such as CsBr₃, are also suitable. Good results are obtained if at least one anhydrous alkali metal bromide or at least one bromide of monovalent or divalent copper is employed.

As a rule, the metal bromides are employed as such; they can, however, also be produced shortly before or during the reaction with the substantially fluorinated alkyl iodides of the formula (I), either from a metal bromide of lower valence, for example cesium monobromide, copper-(I) bromide, iron-(II) bromide and bromine, or from the corresponding metal, for example copper, iron or zinc, and bromine, the alkali and alkaline earth metals being less suitable for the latter process owing to their vigorous reaction with bromine. In this process the bromine is advantageously employed in the stoichiometric amounts necessary for the production of the metal salts containing more bromine, or in smaller amounts. It is also possible to produce metal bromides of a lower valence from the corresponding metal, for example copper or tin, and the metal bromide of higher valence, for example copper-(II) bromide or tin-(IV) bromide.

Either a single metal bromide or a mixture of different metal bromides which differ both in the metal component and also in their valency or in the complex character of the bromide, can be used for the process according to the invention.

The metal bromide or bromides and also, if appropriate, the metal, are advantageously employed in a finely divided form having a large surface area, for example pulverized. During the reaction with the substantially fluorinated alkyl iodide of the formula (I) the reaction mixture is thoroughly mixed, for example by shaking, stirring, grinding, agitation, kneading and similar known methods.

In order to avoid undesirable side reactions, the metal bromide used should as far as possible be free from water. It is advantageous to carry out the reaction in an anhydrous atmosphere of inert gas, for example nitrogen or argon. High-efficiency drying of the metal bromide can be carried out immediately before it is mixed with the substantially fluorinated alkyl iodide, for example by drying under reduced pressure and an elevated temperature, with or without passing an anhydrous inert gas or anhydrous hydrogen bromide gas through or over the metal bromide.

The starting materials to be employed are, as a rule, added to one another completely before the start of the reaction; it is also possible, however, initially to take solely either the substantially fluorinated alkyl iodide or the metal bromide and to add a fraction of the components not taken initially at the start of the reaction and to add further fractions of these components in the course of the reaction.

The reaction, described above, according to the invention is carried out at a temperature of 80° to 450° C., and takes place advantageously under normal atmospheric pressure or under the autogenous pressure of the reaction mixture. The use of higher pressures is, as a rule, not required and represents unnecessary expense. Below 80° C. the reaction generally proceeds too slowly; above 450° C. the formation of undesirable byproducts is increasingly noted.

If CsBr₃ or a similar complex bromide having the anions $Br_3^-$, $IBr_2^-$ or $I_2Br^-$, in particular a complex alkaline metal bromide, is used, it is advantageous to select a temperature in the lower part of the range indicated above, advantageously 100° to 150° C. The same applies if metal bromides of higher valence are produced using bromine during the reaction according to the invention. In all other cases, that is to say if CsBr₃, another complex bromide or bromine is not employed, it is advantageous to select a temperature in the middle or upper part of the temperature range indicated. It is advantageous to carry out the reaction at 220° to 350° C.

The reaction time depends on the temperature used, the starting materials employed and the desired conversion, and is generally 2 to 80 hours; a longer reaction time is possible, but in most cases no additional effect is observed which would justify the increasingly poorer space-time yields. Good results are often obtained at a reaction time of 5 to 20 hours.

When the reaction is complete the reaction mixture is cooled and is either immediately distilled or fractionally distilled or is filtered, and the solid filtered off is washed or dried in order to recover substantially fluorinated alkyl bromide still adsorbed, or water is first added to the reaction mixture, and the phase containing the substantially fluorinated alkyl bromides is separated off and then fractionally distilled, using reduced pressure if required. If iodine—recognizable by a characteristic coloration—is present in the distillate, it can be removed by extraction by shaking or stirring with dilute sodium hydroxide solution.

The substantially fluorinated alkyl bromides prepared by the process according to the invention can be employed in the medicinal sector, for example as contrast agents in examinations using X-rays or ultrasound, for example for rendering tumors visible, for the perfusion of organs and, in an aqueous emulsion, as a blood substitute. Further uses of the substantially fluorinated alkyl bromides are liquids inert at high temperatures and contrast agents for $^{19}F$-nuclear magnetic resonance (NMR) spectral analysis.

In contrast with the known processes, the process according to the invention makes it possible to use low-cost equipment without difficulties in regard to corrosion and without special safety precautions. In comparison with the processes recently suggested, surprisingly good yields of substantially fluorinated alkyl bromides are obtained, as already stated above, although the use of additives, such as catalysts and solvents, which make the process more expensive, is dispensed with. Insofar as byproducts are produced in appreciable amounts in the new process, they can be isolated in a customary manner and used for various purposes. For example, the compounds which can carry a hydrogen atom or a fluorinated alkyl radical instead of the iodine atom in the abovementioned formula (I) are used as heat transfer fluids.

The following examples are intended to illustrate the invention in greater detail.

EXAMPLE 1

12.8 g (0.06 mol) of finely ground cesium bromide of the formula CsBr are put into a bomb tube of capacity 25 cm³ and made of glass, and are subjected to a temperature of 200° C. under a pressure of 10 Pa for 4 hours, in order to remove residual water. After it has cooled to room temperature, 21.85 g (0.04 mol) of perfluorooctyl iodide of the formula $CF_3(CF_2)_7I$ are put into the bomb tube while anhydrous nitrogen is introduced, and the bomb tube is sealed by fusion and shaken for 10 hours at 300° C. 1.5 mol of bromide ions are employed per mol of bound iodine atom in the perfluorooctyl iodide.

When the reaction is complete, the bomb tube is cooled and opened, the liquid organofluorine phase is decanted off and adsorbed organofluorine product is distilled off, at a bottom temperature of up to 250° C., from the residual solid, which consists essentially of cesium bromide and cesium iodide. The organofluorine product distilled off is combined with the decanted product. The 18.8 g thus obtained contain, according to $^{19}$F-NMR spectroscopic and gas chromatographic analysis, 33.9% by weight of $CF_3(CF_2)_7Br$; 62.5% by weight of $CF_3(CF_2)_7I$; 1.7% by weight of $CF_3(CF_2)_7H$ and 1.5% by weight of $CF_3(CF_2)_{14}CF_3$. The yield of $CF_3(CF_2)_7Br$, relative to perfluorooctyl iodide employed, is 31.9%; 53.8% of the perfluorooctyl iodide were recovered.

EXAMPLE 2

140 g of a product which is composed of 80% by weight of cesium tribromide of the formula $CsBr_3$ and 20% by weight of cesium bromide of the formula CsBr, and which has been prepared from anhydrous cesium monobromide and bromine in an exothermic reaction, are put into a glass flask of capacity 250 cm$^3$, equipped with an internal thermometer, a stirrer, a gas inlet tube and a high-efficiency condenser having a drying tube filled with $CaCl_2$ attached. 0.3 mol of cesium tribromide and 0.13 mol of cesium monobromide are employed. 109.2 g (0.2 mol) of perfluorooctyl iodide are introduced into the glass flask while anhydrous nitrogen is passed in, and the mixture in the flask is stirred for 16 hours under normal atmospheric pressure at reflux temperature (100° to 130° C.). 5.15 mol of bromide ions are employed per mol of bound iodine atom. After the completion of the reaction and cooling to room temperature, the contents of the flask are filtered under reduced pressure. The filter residue, consisting essentially of cesium salts, is washed with trichlorotrifluoroethane and is again filtered under reduced pressure. The trichlorotrifluoroethane is removed from the filtrate by distillation, and the residue is combined with the first filtrate. This gives 67.5 g of organofluorine product composed, according to $^{19}$F-NMR spectroscopic analysis, of 95.6% by weight of perfluorooctyl bromide and 4.4% by weight of unreacted perfluorooctyl iodide.

EXAMPLE 3

86.1 g (0.6 mol) of finely ground copper bromide of the formula CuBr are put into a V4A stainless steel shaking autoclave of capacity 250 cm$^3$, and are subjected to a temperature of 200° C. under a pressure of 10 Pa for 3 hours, in order to remove residual water. After the product has cooled to room temperature, 218.4 g (0.4 mol) of perfluorooctyl iodide are introduced while anhydrous nitrogen is passed in, and the autoclave is closed and shaken for 10 hours at 250° C. under the autogenous pressure of the reaction mixture, 0.8 MPa. 1.5 mol of bromide ions are employed per mol of bound iodine atom. After the completion of the reaction the autoclave is cooled and its contents are filtered through a fluted filter. The moist mixture of copper salts obtained as the filter residue is heated in a distillation flask under a pressure of 10$^4$ Pa until a bottom temperature of 150° C. has been reached; condensation of the volatile organofluorine products gives 23.6 g of distillate, which is combined with the original 166.6 g of filtrate. This product contains, according to $^{19}$F-NMR spectroscopic and gas chromatographic analysis, 43.3% by weight of perfluorooctyl bromide; 54.4% by weight of unreacted perfluorooctyl iodide and 1.3% by weight of $CF_3(CF_2)_7H$. The yield of perfluorooctyl bromide, relative to perfluorooctyl iodide employed, is 41.3%.

EXAMPLE 4

13.0 g (0.09 mol) of finely ground copper bromide of the formula CuBr are put into a bomb tube of capacity 25 cm$^3$ and made of glass, and are subjected to a temperature of 200° C. under a pressure of 10 Pa for 4 hours, in order to remove residual water. After the bomb tube has cooled to room temperature, anhydrous nitrogen is passed into it and 16.4 g (0.03 mol) of perfluorooctyl iodide are added, and the bomb tube is sealed by fusion and shaken for 50 hours at 240° to 250° C. 3 mol of bromide ions are employed per mol of bound iodine atom. When the reaction is complete, the bomb tube is opened and the organofluorine products are distilled out of the bomb tube by heating at 200° C. This gives 12.8 g of distillate which, according to analysis by gas chromatography is composed of 97.7% by weight of perfluorooctyl bromide; 1.9% by weight of unreacted perfluorooctyl iodide and 0.3% by weight of $CF_3(CF_2)_7H$. This corresponds to a yield of 83.5% of perfluorooctyl bromide, relative to perfluorooctyl iodide employed.

EXAMPLE 5

The procedure is as indicated in Example 4, but only 8.6 g (0.06 mol) of copper bromide of the formula CuBr instead of 13.0 g are employed and 21.85 g (0.04 mol) of perfluorooctyl iodide instead of 16.5 g are employed. 1.5 mol of bromide ions are used per mol of bound iodine atom. The bomb tube is shaken for 10 hours at 300° C. In the subsequent distillation, as described in Example 4, 18.1 g of distillate are obtained, containing, according to $^{19}$F-NMR spectroscopic and gas chromatographic analysis, 94.5% by weight of perfluorooctyl bromide; 4.1% by weight of unreacted perfluorooctyl iodide and 0.7% by weight of $CF_3(CF_2)_7H$. The yield of perfluorooctyl bromide, relative to perfluorooctyl iodide employed, is 85.7%.

EXAMPLE 6

The procedure is as indicated in Example 4, but the bomb tube is shaken for 10 hours at 300° C. instead of 50 hours at 240° to 250° C. 13.5 g of distillate are obtained, which, according to analysis by gas chromatography, has the following composition: 97.9% by weight of perfluorooctyl bromide; 1.2% by weight of unreacted perfluorooctyl iodide and 0.4% by weight of $CF_3(CF_2)_7H$. The yield of perfluorooctyl bromide, relative to perfluorooctyl iodide employed, is 88.3%.

EXAMPLE 7

6.7 g (0.03 mol) of "anhydrous" copper bromide of the formula $CuBr_2$ and 21.85 g (0.04 mol) of perfluorooctyl iodide are put into a bomb tube of capacity 25 cm$^3$ and made of glass, while anhydrous nitrogen is passed in. 1.5 mol of bromide ions are employed per mol of bound iodine atom. The bomb tube is sealed by fusion and shaken for 10 hours at 300° C. and is then cooled and opened, and the contents are distilled as described in Example 4. The distillate is stirred with dilute sodium hydroxide solution in order to remove the iodine formed, and is then separated from the sodium hydroxide solution and dried. This gives 17.1 g of organofluorine compounds, which, according to analysis by gas chromatography, have the following composition:

95.7% by weight of perfluorooctyl bromide; 0.6% by weight of unreacted perfluorooctyl iodide and 3.3% by weight of CF$_3$(CF$_2$)$_7$H. The comparatively high content of the latter compound indicates that the water content of the CuBr$_2$ purchased as "anhydrous" was not as low as is desirable for the reaction according to the invention.

EXAMPLE 8

5.5 g (0.03 mol) of magnesium bromide of the formula MgBr$_2$ are subjected to a temperature of 200° C. under a pressure of 50 Pa for 3 hours in a bomb tube of capacity of 25 cm$^3$, made of glass, in order to dry the material. After the bomb tube has cooled to room temperature, 17.8 g (0.04 mol) of perfluorohexyl iodide of the formula CF$_3$(CF$_2$)$_5$I are put into it while anhydrous nitrogen is passed in, and the bomb tube is sealed and shaken for 10 hours at 300° C. 1.5 mol of bromide ions are used per mol of bound iodine atom. After the completion of the reaction, the bomb tube is cooled to room temperature and opened, and the volatile organofluorine compounds are removed from the contents by distillation until a bottom temperature of 200° C. is reached. The distillate is treated with dilute sodium hydroxide solution in order to remove small amounts of iodine and is washed again with water, the aqueous phase is separated off and the organofluorine phase is dried. From the latter 13.3 g are obtained, which, according to analysis by gas chromatography, is composed of 76.3% by weight of perfluorohexyl bromide; 0.9% by weight of unreacted perfluorohexyl iodide and 21.2% by weight of a compound of the formula CF$_3$(CF$_2$)$_5$H. The yield of perfluorohexyl bromide, relative to perfluorohexyl iodide employed, is 63.6%. The comparatively high content of hydrogen-containing compound indicates that the magnesium bromide still contained water. Magnesium bromide dried more efficiently would have to give a markedly lower content of hydrogencontaining compound, to the advantage of an improved yield of perfluorohexyl bromide.

EXAMPLE 9

The procedure is as described in Example 8, but 11.3 g (0.06 mol) of silver bromide of the formula AgBr are employed instead of 5.5 g of magnesium bromide. Working up as described in Example 8 gives 14.5 g of organofluorine liquid, which, according to analysis by gas chromatography, is composed of 93.1% by weight of perfluorohexyl bromide; 4.2% by weight of unreacted perfluorohexyl iodide and 2.4% by weight of a compound of the formula CF$_3$(CF$_2$)$_5$H. The yield of perfluorohexyl bromide, relative to perfluorohexyl iodide employed, is 84.6%.

I claim:

1. A process of the preparation of substantially fluorinated alkyl bromides from compounds of the formula $$X-(CF_2)_n-I \qquad (I)$$

in which X is H, F, Cl, Br, I or (CF$_3$)$_2$CF— and n is 2 to 16, which comprises reacting, with good mixing, 1 mole of bound iodine atom in the compound of the formula (I) with 1 to 6 mol of bromide ions which are present in the form of at least one anhydrous salt selected from the group composed of: bromides of metals of groups I a, I b, II a or II b or the periodic table of the elements, CsBr$_3$, MnBr$_2$, FeBr$_2$, FeBr$_3$, CoBr$_2$, NiBr$_2$, SnBr$_2$, PbBr$_2$, TlBr, IrBr, IrBr$_2$, PtBr$_2$ or PtBr$_4$, at 80° to 450° under atmospheric pressure or the autogenous pressure of the reaction mixture so that the iodine in the compound of formula (I) is replaced partly by bromine.

2. The process as claimed in claim 1, wherein the reaction is carried out at 220° to 350° C. without the use of CsBr$_3$.

3. The process as claimed in claim 1, wherein at least one anhydrous alkali metal bromide is employed.

4. The process as claimed in claim 1, wherein a copper bromide is employed.

5. The process as claimed in claim 1, wherein the reaction is carried out at 100° to 150° C. in the presence of CsBr$_3$.

6. The process as claimed in claim 1, wherein at least one compound of the formula (I) in which X is I is employed.

7. The process as claimed in claim 1, wherein at least one compound of the formula (I) in which X is F or (CF$_3$)$_2$CF— is employed.

8. The process as claimed in claim 1, wherein a compound of the formula (I) in which n is 4 to 12 is employed.

* * * * *